United States Patent
Shiflett et al.

(10) Patent No.: US 8,313,558 B2
(45) Date of Patent: Nov. 20, 2012

(54) PROCESS FOR SEPARATION OF TETRAFLUOROETHYLENE FROM CARBON DIOXIDE USING IONIC LIQUIDS

(75) Inventors: Mark Brandon Shiflett, Wilmington, DE (US); Akimichi Yokozeki, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 491 days.

(21) Appl. No.: 12/446,769

(22) PCT Filed: Nov. 8, 2007

(86) PCT No.: PCT/US2007/023496
§ 371 (c)(1),
(2), (4) Date: Apr. 23, 2009

(87) PCT Pub. No.: WO2008/057574
PCT Pub. Date: May 15, 2008

(65) Prior Publication Data
US 2010/0144994 A1    Jun. 10, 2010

Related U.S. Application Data (60) Provisional application No. 60/857,566, filed on Nov. 8, 2006.

(51) Int. Cl.
*B03C 3/00* (2006.01)
*B01D 53/22* (2006.01)

(52) U.S. Cl. .................... 95/64; 95/45; 95/51

(58) Field of Classification Search ............. 518/62.3 R; 203/99; 95/45, 51, 64
See application file for complete search history.

(56) References Cited

U.S. PATENT DOCUMENTS

| | | | |
|---|---|---|---|
| 4,388,812 A | 6/1983 | Clark | |
| 6,155,057 A | 12/2000 | Angell | |
| 6,339,182 B1 | 1/2002 | Munson | |
| 6,579,343 B2 | 6/2003 | Brennecke | |
| 7,208,605 B2 | 4/2007 | Davis | |
| 7,410,586 B2 | 8/2008 | Beste | |
| 7,709,635 B2 | 5/2010 | Davis | |
| 7,744,838 B2 | 6/2010 | Davis | |
| 7,765,823 B2 | 8/2010 | Shiflett | |
| 2004/0035293 A1 | 2/2004 | Davis | |
| 2004/0133058 A1 | 7/2004 | Arlt | |
| 2005/0196671 A1 | 9/2005 | Paonessa | |
| 2005/0196676 A1 | 9/2005 | Singh | |
| 2006/0197053 A1 | 9/2006 | Shiflett et al. | |
| 2006/0251961 A1 | 11/2006 | Olbert et al. | |
| 2007/0019708 A1 | 1/2007 | Shiflett et al. | |
| 2007/0080052 A1 | 4/2007 | Beste et al. | |
| 2007/0089449 A1 | 4/2007 | Gurin | |
| 2007/0131535 A1 | 6/2007 | Shiflett | |
| 2007/0142646 A1 | 6/2007 | Maase | |
| 2007/0144186 A1 | 6/2007 | Shiflett et al. | |
| 2007/0295478 A1 | 12/2007 | Shiflett et al. | |
| 2008/0028777 A1 | 2/2008 | Boesmann et al. | |
| 2008/0153697 A1 | 6/2008 | Shiflett et al. | |
| 2008/0293978 A1 | 11/2008 | Shiflett | |
| 2009/0131728 A1 | 5/2009 | Shiflett | |
| 2010/0095703 A1 | 4/2010 | Jork | |
| 2010/0145073 A1 | 6/2010 | Foo | |
| 2010/0145074 A1 | 6/2010 | Foo | |
| 2010/0152465 A1 | 6/2010 | Davis | |

FOREIGN PATENT DOCUMENTS

| | | |
|---|---|---|
| WO | 9850331 A | 11/1998 |
| WO | 2005016483 A | 2/2005 |
| WO | 2007038363 A | 4/2007 |

OTHER PUBLICATIONS

International Search Report, PCT/US2007/023496, Mar. 25, 2008.
Rogers et al., Ionic Liquids—Solvents of the Future, Science, 2003, vol. 302, pp. 792-793.
Seddon, Ionic Liquids for Clean Technology, J. Chem. Tech. Biotechnol, 1997, vol. 68, pp. 351-356.
Perry's Chemical Engineers Handbook, Section 13, Distillation, 7th Edition, McGraw-Hill, 1997 (Book Not Included).
Enderby, Ionic Liquids Recent Progress and Remaining Problems, J. Phys. Condens, Matter 5, Supp 34B, 1993, B99-B106.
Gordon, Ionic Liquid Crystals:Hexafluorophosphate Salts, J. Mater. Chem, 1998, 8:2627-2636.
Welton, Room-Temperature Ionic Liquids, Chem. Rev. 1999, 99:2071-2084.
Slocum, Multipurpose High-Pressure Phase-Equilibrium Apparatus, Ind. Eng. Chem. Fundam., 1975, vol. 14, No. 2, pp. 126-128.
Schotte, Collection of Phase Equilibrium Data for Separation Technology, Ind. Eng. Chem. Process Des. Dev., 1980, vol. 19, pp. 432-439.
Shiflett, Solubilities and Diffusivities of Carbon Dioxide in Ionic Liquids, Ind. Eng. Chem. Res., 2005, vol. 44, pp. 4453-4464.
S.I. Sandler, Chemical and Engineering Thermodynamics, 3rd Edition, 1999 John Wiley and Sons Inc., New York Chapter 7 (Book Not Included).
Freemantle, Designer Solvents, Ionic Liquids May Boost Clean Technology Development, 1998, Chemical & Engg News, pp. 32-37.
Olivier et al. Nonaqueous Room-Temperature Ionic Liquids: A New Class of Solvents for Catalytic Organic Reactions, 1996, Chem Ind., vol. 68, pp. 249-263.

*Primary Examiner* — Jafar Parsa (57) ABSTRACT

A process for separating tetrafluoroethylene from a mixture comprising tetrafluoroethylene and carbon dioxide by contacting the mixture with at least one ionic liquid.

10 Claims, 2 Drawing Sheets

PROCESS FOR SEPARATION OF TETRAFLUOROETHYLENE FROM CARBON DIOXIDE USING IONIC LIQUIDS

This application claims the benefit of U.S. Provisional Application No. 60/857,566, filed Nov. 8, 2006, which is incorporated in its entirety as a part hereof for all purposes.

TECHNICAL FIELD

This invention relates to a process for separating tetrafluoroethylene from a mixture comprising tetrafluoroethylene and carbon dioxide ($CO_2$).

BACKGROUND

Tetrafluoroethylene ($C_2F_4$, TFE, or FC-1114) is the monomer used to produce polytetrafluoroethylene (PTFE). TFE is highly explosive, flammable, and toxic. In order to prevent TFE from polymerizing unexpectedly while being stored, the TFE is inhibited with either hydrogen chloride (HCl) or carbon dioxide ($CO_2$). TFE and $CO_2$ have similar boiling points and also form an azeotrope, making a mixture of these components difficult if not impossible, to separate (see U.S. Pat. No. 5,345,013). Methods that are currently used for separating TFE from $CO_2$ include membrane permeation, and caustic scrubbing. Following these procedures, the TFE-containing stream can then be processed, for example, to produce a fluoropolymer or copolymer, such as PTFE. The current processes for recovering TFE from $CO_2$ suffer either from high variable cost (caustic scrubbing), high $CO_2$ level in the product (membrane permeation), or multiple unit operations when additional steps are added to address the primary deficiencies.

An alternative approach to separating TFE from $CO_2$ employs extractive distillation or absorption using at least one ionic liquid as an entrainer or absorbent, respectively. U.S. Provisional Application No. 60/719,735 describes the use of separation processes to separate components of mixtures, wherein said mixtures comprise at least one hydrofluorocarbon compound, and may additionally comprise a gas such as $CO_2$. A need nevertheless remains for processes adapted specifically to the separation of TFE from $CO_2$.

SUMMARY

The inventions disclosed herein include processes for the separation of TFE from $CO_2$, processes for the preparation of products into which TFE can be converted, the use of such processes, and the products obtained and obtainable by such processes.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination may be characterized by the absence of the features omitted to form the subcombination; (2) each of the features, individually, included within the combination of any described embodiment; and (3) other combinations of features formed by grouping only selected features of two or more described embodiments, optionally together with other features as disclosed elsewhere herein. Some of the specific embodiments of the processes hereof are as follows:

One such embodiment of the processes hereof provides a process for separating tetrafluoroethylene from a mixture comprising tetrafluoroethylene and carbon dioxide by contacting the mixture with at least one ionic liquid in which carbon dioxide is soluble to a greater extent than tetrafluoroethylene, and separating the tetrafluoroethylene from the mixture. In a further embodiment, the ionic liquid can include a cation selected from the group consisting of pyridinium, pyridazinium, pyrimidinium, pyrazinium, imidazolium, pyrazolium, thiazolium, oxazolium, triazolium, phosphonium, and ammonium, as more particularly described below.

When a separation process hereof is performed by using a technique such as extractive distillation, the process may also involve steps such as adjusting the temperature and/or pressure of the mixture to be separated and/or the feed of ionic liquid.

A further embodiment of the processes hereof provides a process for preparing a fluorinated polymer or copolymer by separating TFE from a mixture thereof with $CO_2$ by contacting the mixture with one or more ionic liquids, recovering the TFE, and subjecting the TFE to a polymerization reaction to prepare a fluorinated polymer or copolymer.

In another embodiment, this invention provides a kit that includes a first container that contains a mixture of TFE and $CO_2$, a second container that contains one or more ionic liquids, and a connector to connect the first container to the second container.

DETAILED DESCRIPTION

The present invention provides a method for separating tetrafluoroethylene from a mixture containing carbon dioxide and tetrafluoroethylene by a separation technique in which at least one ionic liquid is used as a mass separating agent. Techniques useful for performing such a separation include extractive distillation or absorption. In particular, the present invention provides a method for separating tetrafluoroethylene from a mixture comprising tetrafluoroethylene and carbon dioxide comprising contacting the mixture with at least one ionic liquid in which carbon dioxide is soluble to a greater extent than tetrafluoroethylene, and then separating the tetrafluoroethylene from the mixture.

The following definitional structure is provided for certain terminology as employed in this specification:

An "alkane" or "alkane compound" is a saturated hydrocarbon compound having the general formula $C_nH_{2n+2}$, and may be a straight-chain, branched or cyclic compound. A cyclic compound requires a minimum of three carbons.

An "alkene" or "alkene compound" is an unsaturated hydrocarbon compound that contains one or more carbon-carbon double bonds, and may be a straight-chain, branched or cyclic compound. An alkene requires a minimum of two carbons. A cyclic compound requires a minimum of three carbons.

An "aromatic" or "aromatic compound" includes benzene and compounds that resemble benzene in chemical behavior.

An "azeotropic" composition or "azeotrope composition" is a constant-boiling mixture of two or more substances that behaves as a single substance. One way to characterize an azeotropic composition is that the vapor produced by partial evaporation or distillation of the liquid has the same composition as the liquid from which it is evaporated or distilled, i.e., the mixture distills/refluxes without compositional change. Constant-boiling compositions are characterized as azeotropic because they exhibit either a maximum or minimum boiling point, as compared with that of the non-azeotropic mixture of the same components. Azeotropic compositions are also characterized by a minimum or a maximum in the vapor pressure relative to the vapor pressure as a function of composition at a constant temperature.

An "azeotrope-like" composition is a composition that has a constant-boiling characteristic or a tendency not to fractionate upon boiling or evaporation. The composition of the vapor formed is consequently the same as, or substantially the same as, the original liquid composition. During boiling or evaporation, the liquid composition, if it changes at all, changes only to a minimal or negligible extent. An azeotrope-like composition can also be characterized by the area that is adjacent to the maximum or minimum vapor pressure in a plot of composition vapor pressure at a given temperature as a function of mole fraction of components in the composition. A composition is azeotrope-like if, after about 50 weight percent of an original composition is evaporated or boiled off to produce a remaining composition, the change between the original composition and the remaining composition is no more than about 6 weight %, and is typically about 3 weight % or less, relative to the original composition.

A "high-boiling azeotrope" is an azeotropic or azeotrope-like composition that boils at a higher temperature at any given pressure than any one of the compounds that comprise it would separately boil at that pressure. Alternatively, a high-boiling azeotrope is any azeotropic or azeotrope-like composition that has a lower vapor pressure at any given temperature than any one of the compounds that comprise it would separately have at that temperature.

A "low-boiling-azeotrope" is an azeotropic or azeotrope-like composition that boils at a lower temperature at any given pressure than any one of the compounds that comprise it would separately boil at that pressure. Alternatively, a low-boiling azeotrope is any azeotropic or azeotrope-like composition that has a higher vapor pressure at any given temperature than the vapor pressure of any one of the compounds that comprise the azeotrope would separately have at that temperature.

An azeotropic or azeotrope-like composition may also be characterized as a substantially constant-boiling admixture under the following criteria, which may vary according to the conditions:

1) The composition can be defined as an azeotrope of two compounds because the term "azeotrope" is at once both definitive and limitative, and requires effective amounts of those two or more compounds for this unique composition of matter, which can be a constant-boiling composition.

2) At different pressures, the composition of a given azeotrope or azeotrope-like composition will vary at least to some degree, as will the boiling point temperature. Thus, an azeotropic or azeotrope-like composition of two compounds represents a unique type of relationship but with a variable composition, which depends on temperature and/or pressure. Therefore, compositional ranges, rather than fixed compositions, are often used to define azeotropes and azeotrope-like compositions.

3) An azeotrope or azeotrope-like composition of two compounds can be characterized by a boiling point at a given pressure instead of by a specific numerical composition, which is limited by and is only as accurate as the equipment available to perform such an analysis.

Both the boiling point and the weight (or mole) percentages of each component of an azeotropic composition may change when an azeotrope or an azeotrope-like liquid composition is allowed to boil at different pressures. Thus, an azeotropic or an azeotrope-like composition may be defined in terms of the unique relationship that exists among components or in terms of the exact weight (or mole) percentages of each component of the composition characterized by a fixed boiling point at a specific pressure.

The "critical pressure" of a substance is the pressure required to liquefy a gas at its critical temperature, which is the temperature at and above which vapor of the substance cannot be liquefied, regardless of how much pressure is applied.

A "fluorinated ionic liquid" is an ionic liquid having at least one fluorine on either the cation or the anion, or both. A "fluorinated cation" or "fluorinated anion" is a cation or anion, respectively, comprising at least one fluorine atom.

A "halogen" is bromine, iodine, chlorine or fluorine.

A "heteroaryl" group is an aryl group having a heteroatom.

A "heteroatom" is an atom other than carbon in the structure of an alkanyl, alkenyl, cyclic or aromatic compound.

In "high recovery efficiency", greater than 90% by weight and most typically greater than 95% by weight of the TFE or $CO_2$ in a mixture thereof is recovered as a product substantially free of the other.

An "impurity", in a TFE product, is any fluorinated compound other than the TFE; and in a $CO_2$ product, is any inert compound other than the $CO_2$.

An "ionic liquid" is an organic salt that is fluid at about 100° C. or below, as more particularly described in *Science* (2003) 302:792-793.

A "mass separating agent" (MSA) is a compound useful for the separation of components in an azeotropic or constant- or close-boiling mixture. When used in a process such as extractive distillation, the MSA, as an entrainer, interacts selectively with (but does not chemically react with) one or more of the individual components of the mixture. When used in a process such as absorption, the MSA may function as an absorbent that is added to aid in the separation of gaseous components of close-boiling, constant-boiling or azeotropic mixtures by interacting selectively with (but not reacting with) one or more components within the gas mixture. The use and operation of an entrainer or an absorbent is more particularly described in Section 13, "Distillation", in Perry's Chemical Engineers' Handbook, $7^{th}$ Ed., (McGraw-Hill, 1997). An MSA may be used in an "effective amount", which is typically an amount of at least one MSA that, in the presence of a desired product and an impurity, causes the volatility of the impurity to increase or decrease relative to the desired product sufficiently to allow separation by distillation or absorption of the impurity from the desired product. Alternatively, an effective amount of an MSA is an amount that, in the presence of a desired product and an impurity, results in the formation of a lower- or higher-boiling azeotropic or azeotrope-like composition or otherwise causes the volatility of the impurity to increase or decrease relative to the desired product sufficiently to allow separation by distillation or absorption of the impurity from the desired product. An effective amount of an MSA may thus vary depending on the pressure applied to the mixture to be separated in cases where azeotrope or azeotrope-like compositions, or changes in the relative volatility of the components of the mixture, exist.

"Optionally substituted with at least one member selected from the group consisting of", when referring to an alkane, alkene, alkoxy, fluoroalkoxy, perfluoroalkoxy, fluoroalkyl, perfluoroalkyl, aryl or heteroaryl radical or moiety, means that one or more hydrogens on a carbon chain of the radical or moiety may be independently substituted with one or more of the members of a recited group of substituents. For example, a substituted —$C_2H_5$ radical or moiety may, without limitation, be —$CF_2CF_3$, —$CH_2CH_2OH$ or —$CF_2CF_2I$ where the group or substituents consist of F, I and OH.

"Selectivity", "separation factor" or "$\alpha_{ij}$" refers to the ratio of the infinite activity coefficient of component i to the infinite activity coefficient of component j where components i and j are present at an infinite degree of dilution in a mixture, such as a mixture that contains an entrainer and is being subjected to extractive distillation.

"Separating" or "to separate" refers to the removal of a component from a mixture. In various embodiments, separating or to separate may refer to the partial or complete removal of a component from the mixture. If after the partial removal of a component, further purification is required, one or more additional separation steps may be required to achieve complete removal. The initial, and if desired additional, separation steps may include, for example, one or more of the steps of distillation, stripping, rectification, extraction, chromatography, and/or evaporation. Separation may be performed for example by a technique such as extractive distillation wherein an MSA interacts selectively with (but does not react with) one or more components within the mixture, and is typically introduced at an upper feed point of a distillation column, whereas the mixture requiring separation is introduced at the same or preferably a relatively lower feed point of the column than the entraining agent. The MSA passes downwardly through trays or packing located in the column and exits the column bottoms with one or more components of the mixture to be separated. While in the presence of the MSA, at least one of the components to be separated becomes relatively more volatile compared to the other component(s) of the mixture, with that more volatile component of the initial mixture exiting the column overhead. MSAs that are fed to a distillation column at a point equal to, or higher than, the mixture to be separated and which pass down through the column thus enabling a separation by distillation, are also called extractive agents or extractants.

A "vacuum" is a pressure less than 1 bar but greater than $10^{-4}$ bar for practical use in equipment capable of performing a separation process such as extractive distillation.

This invention relates to a process for separating tetrafluoroethylene from $CO_2$ in a mixture thereof. A mixture containing these two components can be obtained from, or provided by, any manufacturing process or source that produces or generates at least one of the components. For example, TFE may be produced by reacting chlorodifluoromethane (HCFC-22 or R-22) in a pyrolysis furnace, and then $CO_2$ may be admixed with the TFE product, typically at a concentration of about 50 weight percent (wt %) TFE relative to the concentration of $CO_2$. The $CO_2$ inhibits the TFE from polymerizing prematurely, which could release a large amount of heat and could lead to an explosion. The mixture comprising TFE and $CO_2$ may additionally comprise small amounts of impurities, such as HCFC-22 or hexafluoropropylene (HFP). $CO_2$ may be obtained commercially from various vendors such as Air Liquide, or can be obtained from the reaction of steam and a hydrocarbon such as methane, a reaction that also produces hydrogen, or produces ammonia if conducted in air.

TFE and $CO_2$, in their separated and pure states have normal boiling points of −75.6 and −78.4° C., respectively. These close boiling points alone would make efficient separation of TFE and $CO_2$ extremely difficult by conventional distillation. However, mixtures of TFE and $CO_2$ also form azeotropic (96 mol % $CO_2$ and 4 mol % TFE at −35° C.) and/or azeotrope-like compositions, which makes their complete separation by conventional distillation next to impossible (see, for example, U.S. Pat. No. 5,345,013). Therefore, separating even the azeotrope composition would require tall and expensive distillation columns, and it would still be extremely difficult to produce substantially pure TFE and $CO_2$ products without substantial loss of the TFE in the $CO_2$.

In a process of this invention, TFE is separated from a mixture thereof with $CO_2$ using an ionic liquid, or a mixture of ionic liquids, as a mass separating agent. Ionic liquids are organic compounds that are liquid at room temperature (approximately 25° C.). They differ from most salts in that they have very low melting points, and they tend to be liquid over a wide temperature range. Many of them are not soluble in non-polar hydrocarbons; are immiscible with water, depending on the anion; and many of them are highly ionizing (but have a low dielectric strength). Ionic liquids have essentially no vapor pressure, most are air and water stable, and they can either be neutral, acidic or basic.

A cation or anion of an ionic liquid useful herein can in principle be any cation or anion such that the cation and anion together form an organic salt that is liquid at or below about 100° C. The properties of an ionic liquid can, however, be tailored by varying the identity of the cation and/or anion. For example, the acidity of an ionic liquid can be adjusted by varying the molar equivalents and type and combinations of Lewis acids used.

Many ionic liquids are formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various Lewis acids or their conjugate bases to form the ionic liquid. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but preferably, the alkyl groups are $C_{1-16}$ groups, since groups larger than this may produce low melting solids rather than ionic liquids. Various triarylphosphines, thioethers and cyclic and non-cyclic quaternary ammonium salts may also been used for this purpose. Counterions that may be used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, zinc trichloride anion, as well as various lanthanum, potassium, lithium, nickel, cobalt, manganese, and other metal-containing anions.

Ionic liquids may also be synthesized by salt metathesis, by an acid-base neutralization reaction or by quaternizing a selected nitrogen-containing compound; or they may be obtained commercially from several companies such as Merck (Darmstadt, Germany) or BASF (Mount Olive, N.J.).

Representative examples of useful ionic liquids are described in sources such as *J. Chem. Tech. Biotechnol.*, 68:351-356 (1997); *Chem. Ind.*, 68:249-263 (1996); *J. Phys. Condensed Matter,* 5: (supp 34B):B99-B106 (1993); *Chemical and Engineering News*, Mar. 30, 1998, 32-37; *J. Mater. Chem.*, 8:2627-2636 (1998); *Chem. Rev.*, 99:2071-2084 (1999); and US 2004/0133058 (which is incorporated as a part hereof). In one embodiment hereof, a library, i.e. a combinatorial library, of ionic liquids may be prepared, for example, by preparing various alkyl derivatives of the quaternary ammonium cation, and varying the associated anions.

Among the ionic liquids that are suitable for use herein to enhance the separation of TFE from $CO_2$ are those that have a lower, and preferably a distinctly lower, solubility and diffusivity for the TFE than the $CO_2$ in the mixture. In one embodiment of this invention, ionic liquids suitable for use herein for such purpose include those having cations described generally by one or more of the following formulae:

Pyridinium

Pyridazinium

Pyrimidinium

Pyrazinium

Imidazolium

Pyrazolium

Thiazolium

Oxazolium

Triazolium

Phosphonium and

-continued

R$^{10}$—N$^{\oplus}$—R$^8$ with R$^7$ above and R$^9$ below

Ammonium wherein $R^1$, $R^2$, $R^3$, $R^4$, $R^5$ and $R^6$ are each independently selected from the group consisting of:

(i) H;
(ii) halogen;
(iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(v) $C_6$ to $C_{20}$ unsubstituted aryl, or $C_3$ to $C_{25}$ unsubstituted heteroaryl having one to three heteroatoms independently selected from the group consisting of O, N, Si and S; and
(vi) $C_6$ to $C_{25}$ substituted aryl, or $C_3$ to $C_{25}$ substituted heteroaryl having one to three heteroatoms independently selected from the group consisting of O, N, Si and S;

wherein said substituted aryl or substituted heteroaryl has one to three substituents independently selected from the group consisting of:

1. —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
2. OH,
3. $NH_2$, and
4. SH; and wherein $R^7$, $R^8$, $R^9$, and $R^{10}$ are each independently selected from the group consisting of:

(vii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(viii) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(ix) $C_6$ to $C_{25}$ unsubstituted aryl, or $C_3$ to $C_{25}$ unsubstituted heteroaryl having one to three heteroatoms independently selected from the group consisting of O, N, Si and S; and
(x) $C_6$ to $C_{25}$ substituted aryl, or $C_3$ to $C_{25}$ substituted heteroaryl having one to three heteroatoms independently selected from the group consisting of O, N, Si and S;

wherein said substituted aryl or substituted heteroaryl has one to three substituents independently selected from the group consisting of:

(1) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH, (2) OH,
(3) NH$_2$, and
(4) SH; and
wherein optionally at least two of R$^1$, R$^2$, R$^3$, R$^4$, R$^5$, R$^6$, R$^7$, R$^8$, R$^9$, and R$^{10}$ can together form a cyclic or bicyclic alkanyl or alkenyl group.

In another embodiment, ionic liquids suitable for use herein include those having fluorinated cations wherein at least one member selected from R$^1$, R$^2$, R$^3$, R$^4$, R$^5$, R$^6$, R$^7$, R$^8$, R$^9$ and R$^{10}$, as described above, comprises F$^-$.

In a further embodiment, an ionic liquid suitable for use herein may have an anion selected from the group consisting of [CH$_3$CO$_2$]$^-$, [HSO$_4$]$^-$, [CH$_3$OSO$_3$]$^-$, [C$_2$H$_5$OSO$_3$]$^-$, [AlCl$_4$]$^-$, [CO$_3$]$^{2-}$, [HCO$_3$]$^-$, [NO$_2$]$^-$, [NO$_3$]$^-$, [SO$_4$]$^{2-}$, [PO$_4$]$^{3-}$, [HPO$_4$]$^{2-}$, [H$_2$PO$_4$]$^-$, [HSO$_3$]$^-$, [CuCl$_2$]$^-$, Cl$^-$, Br$^-$, I$^-$, SCN$^-$; and preferably any fluorinated anion. Representative fluorinated anions suitable for use herein include [Bf$_4$]$^-$, [BF$_3$CF$_3$]$^-$, [BF$_3$C$_2$F$_5$]$^-$, [PF$_6$]$^-$, [PF$_3$(C$_2$F$_5$)$_3$]$^-$, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$; and F$^-$. In another embodiment, an ionic liquid herein may comprise a cation selected from the group consisting of pyridinium, pyridazinium, pyrimidinium, pyrazinium, imidazolium, pyrazolium, thiazolium, oxazolium, triazolium, phosphonium, and ammonium as defined above; and an anion selected from the group consisting of [CH$_3$CO$_2$]$^-$, [HSO$_4$]$^-$, [CH$_3$OSO$_3$]$^-$, [C$_2$H$_5$OSO$_3$]$^-$, [AlCl$_4$]$^-$, [CO$_3$]$^{2-}$, [HCO$_3$]$^-$, [NO$_2$]$^-$, [NO$_3$]$^-$, [SO$_4$]$^{2-}$, [PO$_4$]$^{3-}$, [HPO$_4$]$^{2-}$, [H$_2$PO$_4$]$^-$, [HSO$_3$]$^-$, [CuCl$_2$]$^-$, Cl$^-$, Br$^-$, I$^-$, SCN$^-$; and any fluorinated anion. In yet another embodiment, an ionic liquid herein may comprise a cation selected from the group consisting of pyridinium, pyridazinium, pyrimidinium, pyrazinium, imidazolium, pyrazolium, thiazolium, oxazolium, triazolium, phosphonium, and ammonium as defined above; and an anion selected from the group consisting of [BF$_4$]$^-$, [BF$_3$CF$_3$]$^-$, [BF$_3$C$_2$F$_5$]$^-$, [PF$_6$]$^-$, [PF$_3$(C$_2$F$_5$)$_3$]$^-$, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$, and F$^-$.

In still another embodiment, an ionic liquid herein may comprise a cation selected from the group consisting of pyridinium, pyridazinium, pyrimidinium, pyrazinium, imidazolium, pyrazolium, thiazolium, oxazolium, triazolium, phosphonium, and ammonium as defined above, wherein at least one member selected from R$^1$, R$^2$, R$^3$, R$^4$, R$^5$, R$^6$, R$^7$, R$^8$, R$^9$, and R$^{10}$ comprises F$^-$; and an anion selected from the group consisting of [CH$_3$CO$_2$]$^-$, [HSO$_4$]$^-$, [CH$_3$OSO$_3$]$^-$, [C$_2$H$_5$OSO$_3$]$^-$, [AlCl$_4$]$^-$, [CO$_3$]$^{2-}$, [HCO$_3$]$^-$, [NO$_2$]$^-$, [NO$_3$]$^-$, [SO$_4$]$^{2-}$, [PO$_4$]$^{3-}$, [HPO$_4$]$^{2-}$, [H$_2$PO$_4$]$^-$, [HSO$_3$]$^-$, [CuCl$_2$]$^-$, Cl$^-$, Br$^-$, I$^-$, SCN$^-$, and any fluorinated anion. In still another embodiment, an ionic liquid herein may comprise a cation selected from the group consisting of pyridinium, pyridazinium, pyrimidinium, pyrazinium, imidazolium, pyrazolium, thiazolium, oxazolium, triazolium, phosphonium, and ammonium as defined above, wherein at least one member selected from R$^1$, R$^2$, R$^3$, R$^4$, R$^5$, R$^6$, R$^7$, R$^8$, R$^9$, and R$^{10}$ comprises F$^-$; and an anion selected from the group consisting of [BF$_4$]$^-$, [BF$_3$CF$_3$]$^-$, [BF$_3$C$_2$F$_5$]$^-$, [PF$_6$]$^-$, [PF$_3$(C$_2$F$_5$)$_3$]$^-$, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$, and F$^-$.

In still another embodiment, an ionic liquid suitable for use in this invention may include those having:

a) imidazolium as the cation, and an anion selected from the group consisting of [BF$_4$]—, [BF$_3$CF$_3$]—, [BF$_3$C$_2$F$_5$]—, [PF$_6$]—, [PF$_3$(C$_2$F$_5$)$_3$]—, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$, and [CH$_3$OSO$_3$]$^-$;

b) 1-butyl-3-methylimidazolium as the cation, and an anion selected from the group consisting of [BF$_4$]—, [BF$_3$CF$_3$]—, [BF$_3$C$_2$F$_5$]—, [PF$_6$]—, [PF$_3$(C$_2$F$_5$)$_3$]—, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$, and [CH$_3$OSO$_3$]$^-$;

c) 1-ethyl-3-methylimidazolium as the cation, and an anion selected from the group consisting of [BF$_4$]—, [BF$_3$CF$_3$]—, [BF$_3$C$_2$F$_5$]—, [PF$_6$]—, [PF$_3$(C$_2$F$_5$)$_3$]—, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$, and [CH$_3$OSO$_3$]$^-$;

d) 1-ethyl-3-methylimidazolium as the cation, and [(CF$_3$CF$_2$SO$_2$)$_2$N]$^-$, [PF$_6$]$^-$, or [HCF$_2$CF$_2$SO$_3$]$^-$ as the anion;

e) 1,3-dimethylimidazolium as the cation, and an anion selected from the group consisting of [BF$_4$]—, [BF$_3$CF$_3$]—, [BF$_3$C$_2$F$_5$]—, [PF$_6$]—, [PF$_3$(C$_2$F$_5$)$_3$]—, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$, and [CH$_3$OSO$_3$]$^-$.

In various other embodiments of this invention, an ionic liquid formed by selecting any of the individual cations described or disclosed herein, and by selecting any of the individual anions described or disclosed herein, may be used for the purpose of effecting or enhancing the separation of TFE from CO$_2$. Correspondingly, in yet other embodiments, a subgroup of ionic liquids formed by selecting (i) a subgroup of any size of cations, taken from the total group of cations described and disclosed herein in all the various different combinations of the individual members of that total group, and (ii) a subgroup of any size of anions, taken from the total group of anions described and disclosed herein in all the various different combinations of the individual members of that total group, may be used for the purpose of effecting or enhancing the separation of TFE from CO$_2$. In selecting an individual ionic liquid, or in forming a subgroup of ionic liquids by making selections as aforesaid, the ionic liquid or subgroup may be used in the absence of the members of the group(s) of cations and/or anions that are omitted from the total group(s) thereof to make the selection; and, if desirable, the selection may thus be made in terms of the members of the total group(s) that are omitted from use rather than the members of the group(s) that are, by the selection, included for use.

In the process of this invention, TFE is separated from a mixture thereof with $CO_2$ by contacting the mixture with an ionic liquid in which $CO_2$ is soluble to a greater extent than TFE. This is advantageous because the difference in solubility facilitates the use of a separation technique that removes the lower-solubility TFE component from the mixture, such as by volatilization, but removes the more-soluble $CO_2$ component (along with the TFE) to a more limited extent, and preferably does not remove $CO_2$ at all. To the extent that it is soluble in the ionic liquid, the $CO_2$ will tend to remain in the mixture as the TFE is being removed therefrom.

Separation techniques useful for performing the process of this invention include, for example, techniques such as extractive distillation and absorption. In extractive distillation, as in conventional distillation, at least one component of the mixture is caused, through temperature and pressure control, to be volatilized in a column, and the volatilized component is captured in a separate stream in which it is condensed apart from, and is thus removed from, the mixture. At least a portion of this condensed stream can be returned to the top of the column as reflux, and the remainder recovered as product or for optional processing. The ratio of the condensed material which is returned to the top of the column as reflux to the material removed as distillate is referred to as the reflux ratio. The compounds exiting the column as the bottoms stream can be passed to a stripper or second distillation column for further separation, and, if desired, compounds recovered from the bottoms may then be recycled back to the first distillation column for reuse.

The specific conditions applicable to the use of distillation in this invention depend on parameters such as the diameter of the distillation column, location of feed points, and the number of separation stages in the column. The operating pressure of the distillation system may range from about vacuum to about 3.45 MPa (about 500 psia), and may be adjusted in view of the temperatures of the heating and cooling media available. Normally, increasing the reflux ratio results in increased distillate stream purity, but generally the reflux ratio ranges between 1/1 to 200/1. The temperature of the condenser, which is located adjacent to the top of the column, is normally sufficient to substantially fully condense the distillate that is exiting from the top of the column, or is that temperature required to achieve the desired reflux ratio by partial condensation.

In extractive distillation, there is added to the mixture being separated in the column a miscible, high-boiling, relatively nonvolatile MSA that has low latent heat of vaporization, does not form an azeotrope with any of the components in the mixture, and does not chemically react with any of the components in the mixture. The MSA is specially chosen to interact differently with the various components of the mixture, thereby altering their relative volatilities and "breaking" the azeotrope in which they would otherwise exist. The MSA is thus chosen herein to be an ionic liquid in which the $CO_2$ component of the mixture is more soluble, and preferably much more soluble, than the TFE component of the mixture. The TFE component, being less soluble in the MSA may, as a result, be more easily volatilized and separated from the mixture than the $CO_2$ component, which is more soluble in the MSA, which is functioning as an entrainer. The tendency that the components of an azeotrope would ordinarily have to volatilize in the essentially the same compositional ratio as they possess in liquid from is thus altered by the presence of the MSA, which, by solubilizing the $CO_2$ component of the mixture to a greater extent than the TFE component, causes a corresponding change in the compositional content of the stream of volatiles liberated from the mixture at a selected temperature and pressure. The TFE component is then removed from the mixture at the selected temperature and pressure as vapor in much higher concentration than the $CO_2$ component, and is preferably removed in essentially pure form uncontaminated with $CO_2$. The more soluble, less volatile $CO_2$ component remains in the mixture with the MSA, and another criterion for selection of the MSA is that it be an ionic liquid that is easily separated from $CO_2$.

In various embodiments, mixtures of ionic liquids as MSAs may also be useful for achieving a desired extent of separation. In one embodiment, a mixture of MSAs may be selected wherein one MSA has a high selectivity for the $CO_2$ component, and the other MSA has a high capacity to solubilize the $CO_2$.

Figure 1:
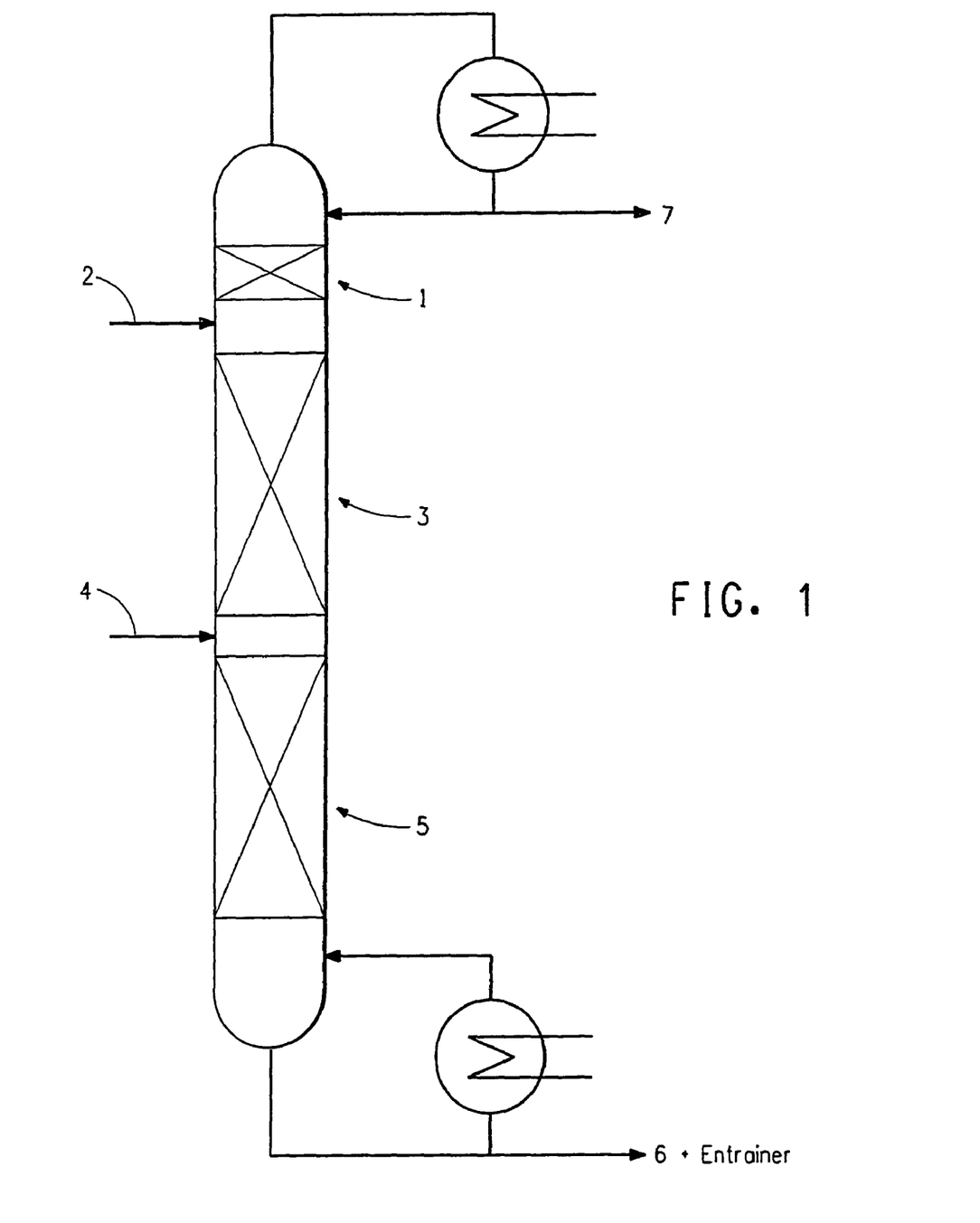
FIG. 1 is a schematic diagram of a simple extractive distillation system.
Figure 2:
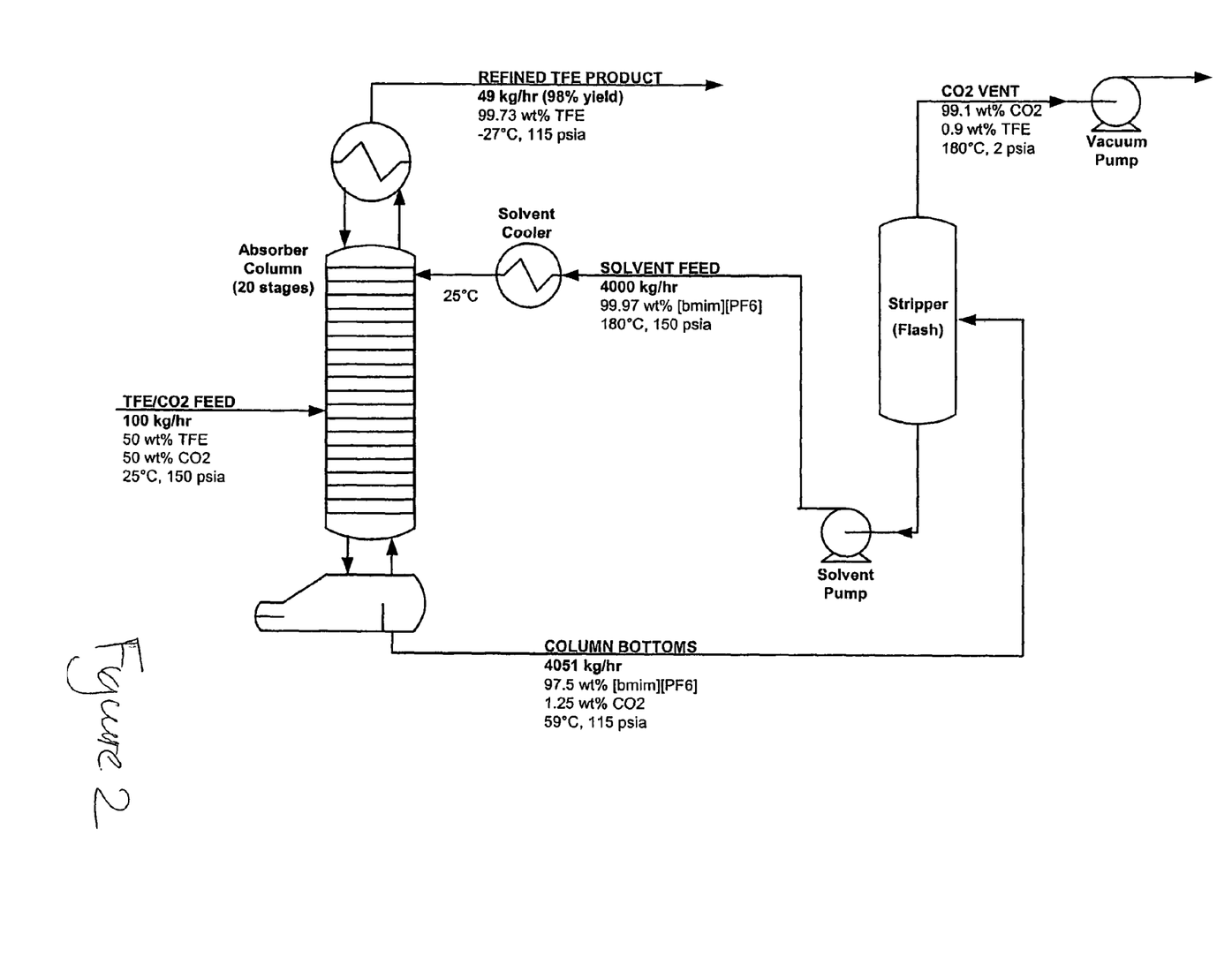
FIG. 2 is a schematic diagram of a simple absorption system.

When the separation process of this invention is performed by extractive distillation, it may be advantageously performed in a distillation column such as is shown in the schematic diagram of FIG. 1. In the column of FIG. 1, separator elements 1 are used for the separation from the MSA of the top product, which is the mixture component that is made more volatile by the presence of the MSA in the mixture. Use of an ionic liquid as the MSA has the advantage of essentially eliminating the presence of the MSA in the overhead product 7 because of the negligible volatility of an ionic liquid.

The flow of the MSA enters at inlet 2, which is preferably located in the enriching section close to the top of the column below the condenser, or at the bottom of the rectifying section, wherein any amount of the MSA that has unexpectedly volatilized is separated from the TFE component of the mixture. The ionic liquid as MSA then proceeds in a countercurrent flow direction downward in the column relative to the upward flow of the components of the mixture to be separated, especially the lower-solubility TFE. The mixture enters at inlet 4, above the stripping section, where any of the TFE component that is still admixed with the MSA is finally vaporized. The inlet feed of the mixture to be separated may be in liquid or gaseous form, and, if the mixture is in liquid form when fed into the column, at least the TFE component thereof will be volatilzed by the temperature and pressure conditions of the column, which will have been selected for that purpose. The vapors moving upward in the column are continuously enriched in content of the TFE component of the mixture, and the liquid moving downward in the column is continuously depleted in content of that component.

Separator elements 3 and 5 contain a useful number of stages along the height of the column at which there is thorough gas-liquid contacting, which is desirable for the purpose of obtaining extensive separation of the TFE component, which exits the column as the overhead product 7, from the $CO_2$ component, which exits the column together with the MSA as the bottom product 6.

Separator elements can be either plates, or ordered or disordered packings. In either event, the purpose is to provide a downward cascade of the MSA, as a liquid entrainer, to contact the rising stream of vaporized high-volatility component. If plates are used, the liquid may flow over the edge of one plate onto another, or the liquid may flow through the same holes in the plates through which the volatilized component rises. In either case, the objective is to achieve maximum residence time of gas-liquid contact consistent with providing a rate of upward vapor flow that is high enough to prevent the column from being flooded by the downcoming liquid, but is not so high that the vapor is pushed out of the column without sufficient time to contact the liquid.

There is, in terms of the amount of the mixture to be separated, a minimum amount of the MSA that is needed to "break" the azeotropic, or the constant- or close-boiling, characteristics of the mixture, and enable the separation of the TFE component from the mixture in a yield and at a rate that is commercially feasible. In a ratio of the amount of the feed of MSA to the amount of feed of the mixture, where the amount of MSA used in the ratio is the minimum amount described above, the value of the ratio may in various embodiments be set in a range such as about 2 to about 4. In other embodiments, feed ratios above 5 may be found to offer no particular advantage in terms of being able to reduce the number of stages in a column. In other embodiments, however, feed ratios above or below the ranges described above may be appropriate depending on the ability of the MSA to preferentially solubilize the $CO_2$ as compared to the TFE. Typically, an increase in the feed rate of the MSA relative to the feed rate of the mixture to be separated, other things being equal, does cause an increase in the purity of the TFE product to be recovered with regard to the remaining presence of $CO_2$.

As the separation progresses to conclusion, the MSA is in another step removed from the column, as bottoms with the $CO_2$ component, and the MSA is recycled back to the column for re-entry therein at inlet 2. The MSA may be separated from the bottom product 6 using various separating operations including regeneration by simple evaporation. Thin film evaporators, such as falling-film or rotary evaporators, are commonly used for continuous evaporation. In discontinuous concentration processes, two evaporator stages are run alternately so that regenerated ionic liquid, as the MSA, can be returned continuously to the distillation column. The MSA can also be regenerated by means of a stripping column since the vapor pressure of the ionic liquid is essentially zero. A vacuum pump can be used to aid in the separation by lowering the pressure and decreasing the heat input required to degas the ionic liquid. An alternative means of recovering an ionic liquid as MSA takes advantage of the fact that many ionic liquids can solidify below 0° C. In these cases, low cost separation of the ionic liquid can be achieved by cooling to form a solid phase. The bottom product can also be precipitated using techniques such as cooling, evaporative, or vacuum crystallization.

An absorption process is typically run with a column similar to that used in a distillation process except that when contact alone between the ionic liquid MSA and the mixture is sufficient to drive the $CO_2$ component to dissolve in the ionic liquid, a reflux condenser and a reboiler may not be needed. The liquid MSA is added at or toward the top of the column, and the vaporized mixture contacts the liquid as it moves up the column while the liquid is moving down. Where, however, the MSA does have some degree of volatility itself, it may be desirable to add a reflux condenser. Where, at the column operating pressure, reflux occurs at an undesirably low temperature, a column with a reboiler may be used.

These and other aspects of extractive distillation and absorption are further discussed in sources such as *Perry's Chemical Engineers' Handbook*, $7^{th}$ Ed. (Sections 13 and 14, McGraw-Hill, 1997).

The ability to separate a binary mixture of two components i and j can be determined by calculating their selectivity. The closer the selectivity is to the value of one, the more difficult it is for the components of the mixture to be separated by conventional distillation. Therefore, an extractive distillation or absorption method may be used to enhance the separation efficiency. In extractive distillation or absorption, an MSA influences the separation by selectively absorbing or dissolving one or more of the components in the mixture. Where, as in this invention, an ionic liquid is used as an MSA, the selectivity of an ionic liquid for a binary mixture composed of i and j is defined as the ratio of the infinite activity coefficient of component i to the infinite activity coefficient of component j, where components i and j are present at an infinite degree of dilution in the ionic liquid MSA. In general the selectivity can be greater than or less than 1 depending on whether the low boiler or high boiler is in the numerator. Normally the low boiler is placed in the numerator so that the selectivity is shown as a value greater than 1. In order to achieve effective separation, a selectivity of greater than about 1.0 is generally required. In one embodiment of the invention, the addition of an ionic liquid to the mixture provides a selectivity greater than about 1.5; and in other embodiments of the invention, the addition of an ionic liquid to the mixture provides a selectivity greater than about 2, greater than about 5, greater than about 10, or greater than about 20.

When the separation of this invention is performed by distillation, the individual components of the mixture may have respective concentrations ranging from about 0.05 to about 99.95 mole percent, relative to the total weight of all components in the mixture plus the MSA, depending on their location at any particular time in the column. At any particular time in the process and/or location in the column, the components may be subjected to a temperature in the range of from the reboiler temperature to the condenser temperature, and a pressure in the range of from vacuum to the critical pressure. Separation processes operate at varying feed, reboiler and condenser temperatures depending on the appropriate conditions for optimum separation. A typical separation process might operate with a condenser and/or feed composition chilled by water to a temperature of about 5 to about 10° C., or chilled by brine or ethylene glycol to even lower temperatures of about 0 to about −40° C. In some cases, if the column operates at close to the normal boiling point of a compound at about 1 atmosphere pressure, the feed and/or the condenser composition may be cooled to an even lower temperatures of about −40 to about −80° C. The reboiler can operate over a wide temperature range depending on the operating pressure of the column and the identity of the compound(s) being separated, which in the case of a fluorinated compound such as TFE could be a temperature in the range of from about −80 to about 240° C. The process thus involve steps such as adjusting, by raising or lowering, the temperature and/or pressure of the mixture and/or the feed of ionic liquid as needed to achieve the desired separation.

The separation process of this invention may also be performed by the use of a kit, which is another embodiment of this invention. A kit, according to this invention, will, for example, include a first container that contains a mixture of TFE and $CO_2$, a second container that contains one or more ionic liquids, and a connector to connect the first container to the second container. A suitable container may be a cylindrical metal tank or other pressure vessel, and a suitable connector may be a hose or tube. The first container includes an outlet, and the second container includes an inlet and an outlet The contents of the first container will typically be pressurized since some or all of the contents of the first container are to be passed through the second container.

For that purpose, the connecter is connected to the outlet of the first container and to the inlet of the second container, and some or all of the contents of the first container are introduced into the second container. After some or all of the contents of the first container have passed through the second container, they exit the second container through the outlet thereof. For example, some or all of the contents of the first container may be bubbled through the second container, and for such purpose the inlet on the second container may be at the bottom thereof, and the outlet will be at the top. In other embodiments, however, first container contents may be introduced at other locations on the second container and/or may be introduced by methods such as injection or pouring. In its interior, the second container includes means for contacting the TFE/$CO_2$ mixture received from the first container with the ionic liquid residing within the second container. Such contacting means may include perforated piping, spray heads, nozzles, blades, paddles, screws or pumps.

When the connector is attached between the containers, and some or all of the TFE/$CO_2$ mixture in the first container is passed into and through the second container, the $CO_2$ in the mixture is absorbed into the ionic liquid, and purified TFE is released from the outlet of the second container. If desired, the TFE produced by separation of it within the second container from the mixture with $CO_2$ may be used to prepare a fluorinated polymer or copolymer. Another embodiment of this invention is consequently a process for preparing a fluorinated polymer or copolymer by separating TFE from a mixture thereof with $CO_2$ by contacting the mixture with one or more ionic liquids, recovering the TFE, and subjecting the TFE to a polymerization reaction to prepare a fluorinated polymer or copolymer. A fluorinated polymer or copolymer may be produced by a process such as emulsion polymerization under pressure using free radical catalysts such as peroxides or azo compounds, or by other suitable catalysts and conditions selected from those known in the art. The polymer may be a homopolymer such as PTFE; or a copolymer prepared from TFE and monomers such as ethylene or other alpha-olefins; other unsaturated fluorocarbons, hydrofluorocarbons or hydrofluorochlorocarbons; an acrylate; or various vinyl compounds such as vinyl acetate.

The following examples are presented to illustrate the operation of this invention and to assist the artisan in making and using the same. These examples are not intended in any way to limit the scope of the disclosure or the appended claims. In this work, selectivities are used in Example 1 to illustrate the extent to which TFE can be separated from $CO_2$. Example 2 uses a process simulation program (ASPEN Plus®, Aspen Technology, Inc., Cambridge Mass.) to model the separation of TFE and $CO_2$ by extractive distillation using the ionic liquid [bmim][$PF_6$] as an MSA.

General Methods and Materials

1-Butyl-3-methylimidazolium hexafluorophosphate ([bmim][$PF_6$], $C_8H_{15}N_2F_6P$, molecular weight 284 g mol$^{-1}$), was obtained from Fluka Chemika (and may, similarly, be obtained from Sigma-Aldrich, St. Louis, Mo.) with a purity of >97%. Tetrafluoroethylene (TFE, FC-1114, $C_2F_4$, molecular weight 100.02 g mol$^{-1}$) was obtained from DuPont Fluorochemicals (Wilmington, Del.), with a minimum purity of 99.99%. Carbon dioxide ($CO_2$, molecular weight 44.01 g mol$^{-1}$), was obtained from MG Industries (Allentown, Pa.) with a minimum purity of 99.998%.

The syntheses of non-commercially available anions (potassium 1,1,2,2-tetrafluoroethanesulfonate, potassium-1,1,2-trifluoro-2-(perfluoroethoxy)ethanesulfonate, potassium-1,1,2-trifluoro-2-(trifluoromethoxy)ethanesulfonate, and sodium 1,1,2,3,3,3-hexafluoropropanesulfonate); and ionic liquids (1-butyl-2,3-dimethylimidazolium 1,1,2,2-tetrafluoroethanesulfonate, 1-butyl-methylimidazolium 1,1,2,2-tetrafluoroethanesulfonate, 1-ethyl-3-methylimidazolium 1,1,2,2-tetrafluoroethane sulfonate, 1-ethyl-3-methylimidazolium 1,1,2,3,3,3-hexafluoropropanesulfonate, 1-hexyl-3-methylimidazolium 1,1,2,2-tetrafluoroethanesulfonate, 1-dodecyl-3-methylimidazolium 1,1,2,2-tetrafluoroethanesulfonate, -hexadecyl-3-methylimidazolium 1,1,2,2-tetrafluoroethanesulfonate, 1-octadecyl-3-methylimidazolium 1,1,2,2-tetrafluoroethaneulfonate, 1-propyl-3-(1,1,2,2-TFES) imidazolium 1,1,2,2-tetrafluoroethanesulfonate, 1-butyl-3-methylimidazolium 1,1,2,3,3,3-hexafluoropropanesulfonate, 1-butyl-3-methylimidazolium 1,1,2-trifluoro-2-(trifluoromethoxy)ethanesulfonate, 1-butyl-3-methylimidazolium 1,1,2-trifluoro-2-(perfluoroethoxy)ethanesulfonate, tetradecyl(tri-n-butyl)phosphonium 1,1,2,3,3,3-hexafluoropropanesulfonate, tetradecyl(tri-n-hexyl)phosphonium 1,1,2-trifluoro-2-(perfluoroethoxy)ethanesulfonate, tetradecyl(tri-n-hexyl)phosphonium 1,1,2-trifluoro-2-(trifluoromethoxy)ethanesulfonate, 1-ethyl-3-methylimidazolium 1,1,2,2-tetrafluoro-2-(pentafluoroethoxy)sulfonate, and tetrabutylphosphonium 1,1,2-trifluoro-2-(perfluoroethoxy)ethanesulfonate) is described in U.S. Patent Application No. 60/719,735, which is incorporated in its entirety as a part hereof for all purposes.

TFE solubility measurements were made using a glass equilibrium cell [E. W. Slocum, *Ind. Eng. Chem. Fundam.* (1975) 14, 126]. The glass equilibrium cell has a known volume and is agitated so that the upper phase (gas or liquid) mixes into the lower liquid phase. A known amount of ionic liquid is loaded into the cell and evacuated under heating to degas and remove any residual water in the ionic liquid. Knowing the density of the ionic liquid, the volume of the ionic liquid can be calculated, and the difference from the initial glass cell volume used to calculate the vapor space volume. A known amount of gas is fed into the cell and the temperature is held constant with a circulating oil bath. The pressure of the cell is measured and recorded. When the pressure is determined to no longer change, the cell is at equilibrium and the amount of gas absorbed is calculated by taking into account the amount of gas in the equilibrium cell vapor space. Further discussion of this equipment and procedure is available in W. Schotte, *Ind. Eng. Chem. Process Des. Dev.* (1980) 19, 432-439.

$CO_2$ solubility measurements were made using a gravimetric microbalance (Hiden, IGA 003, Hiden Isochema Ltd., Warrington, UK). The microbalance consists of an electrobalance with sample and counterweight components inside a stainless steel pressure-vessel. The balance has a weigh range of 0-100 mg with a resolution of 0.1 μg. An enhanced pressure stainless steel (SS316LN) reactor capable of operation to 2.0 MPa and 100° C. was installed. Approximately 60 mg of ionic liquid sample was added to the sample container and the reactor was sealed. The sample was dried and degassed by first pulling a course vacuum on the sample with a diaphragm pump (Pfeiffer, model MVP055-3, Asslar, Germany) and then fully evacuating the reactor to $10^{-9}$ MPa with a turbopump (Pfeiffer, model TSH-071). While under deep vacuum, the sample was heated to 75° C. for 10 h with an external water jacket connected to a remote-controlled constant-temperature bath (Huber Ministat, model cc-S3, Offenburg, Germany). A 30 percent ethylene glycol and 70 percent water mixture by volume was used as the recirculating fluid with a temperature range of 5 to 90° C. The sample mass slowly decreased as residual water and gases are removed. Once the mass had stabilized for at least 60 min, the sample dry mass was recorded. The IGA003 can operate in both dynamic and static mode. Dynamic mode operation provides a continuous flow of gas (max. 500 cm$^3$ min$^{-1}$) past the sample and the exhaust valve controls the set-point pressure.

Static mode operation introduces gas into the top of the balance away from the sample and both the admittance and exhaust valves control the set-point pressure. All absorption measurements were performed in static mode. The sample temperature was measured with a type K thermocouple with an accuracy of ±0.1° C. The thermocouple was located inside the reactor next to the sample container. The water jacket maintained the set-point temperature automatically to within a typical regulation accuracy of ±0.1° C. Four isotherms (at 10, 25, 50, and 75° C.) were measured beginning with 10° C. Once the desired temperature was achieved and stable, the admittance and exhaust valves will automatically open and close to adjust the pressure to the first set-point. Pressures from $10^{-10}$ to $10^{-2}$ MPa were measured using a capacitance manometer (Pfeiffer, model PKR251), and pressures from $10^{-2}$ to 2.0 MPa were measured using a piezo-resistive strain gauge (Druck, model PDCR4010, New Fairfield, Conn.). Regulation maintained the reactor pressure set-point to within ±4 to 8 kPa. The pressure ramp rate was set at 200 kPa min$^{-1}$, and the temperature ramp rate was set at 1° C. min$^{-1}$. The upper pressure limit of the stainless steel reactor was 2.0 MPa, and several isobars up to 2.0 MPa (i.e. 0.1, 0.5, 1, 4, 7, 10, 13, 15, and 20 bar) were measured. To ensure sufficient time for gas-liquid equilibrium, the ionic liquid samples were maintained at set-point for a minimum of 3 h with a maximum time-out of 12 h. Further discussion of this equipment and procedure is available in M. B. Shiflett and A. Yokozeki, *Ind. Eng. Chem. Res.* (2005) 44(12), 4453-4464.

EXAMPLE 1

Separation of a Mixture Containing Tetrafluoroethylene (TFE) and Carbon Dioxide ($CO_2$)

This example addresses thermodynamic properties at the infinite dilution state. Activity coefficients at infinite dilution $\gamma^\infty$ were analyzed for TFE and $CO_2$ in [bmim][$PF_6$].

Solubility (PTx) data for TFE and $CO_2$ in [bmim][$PF_6$] are summarized in Examples 3 and 4. Data have been correlated with the Non-Random-Two-Liquid (NRTL) solution model.

The NRTL activity coefficient ($\gamma_i$) model for a binary system is given by:

$$\ln \gamma_1 = x_2^2 \left[ \tau_{21} \left( \frac{G_{21}}{x_1 + x_2 G_{21}} \right)^2 + \frac{\tau_{12} G_{12}}{(x_2 + x_1 G_{12})^2} \right], \quad (1)$$

$$\ln \gamma_2 = x_1^2 \left[ \tau_{12} \left( \frac{G_{12}}{x_2 + x_1 G_{12}} \right)^2 + \frac{\tau_{21} G_{21}}{(x_1 + x_2 G_{21})^2} \right], \quad (2)$$

where $G_{12} \equiv \exp(-\alpha \tau_{12})$, and $G_{21} \equiv \exp(-\alpha \tau_{21})$, $\tau_{12}$ and $\tau_{21}$: adjustable binary interaction parameters. (3)

$\alpha = 0.2$ (assumed to be a constant of 0.2 in this work). (4)

The temperature-dependent binary interaction parameter ($\tau_{ij}$) is modeled by:

$$\tau_{ij} = \tau_{ij}^{(0)} + \tau_{ij}^{(1)}/T. \quad (5)$$

Vapor liquid equilibria (VLE) are obtained by solving the following equations:

$$y_i P \Phi_i = x_i \gamma_i P_i^S, \text{ (i=1 for TFE and i=2 for ionic liquid)} \quad (6)$$

In the present system, it can be assumed that $P_2^S \approx 0$ and $y_2 \approx 0$ (or $y_1 \approx 1$). Then, eq 6 becomes only one equation with i=1, and the correction factor for non-ideality, $\Phi_1$, can be written as:

$$\Phi_1 = \exp\left[ \frac{(B_{11} - \overline{V}_1)(P - P_1^S)}{RT} \right]. \quad (7)$$

The second virial coefficient, $B_{11}(T)$, of pure species 1 can be calculated with proper equation-of-state models, and the saturated molar liquid volume, $\overline{V}_1(T)$, is calculated using the method described in Shiflett, M. B.; Yokozeki, A. Solubility and Diffusivity of Hydrofluorocarbons in Room-Temperature Ionic Liquids. *AIChE J.* (2006), 52, 1205. The vapor pressure of pure species 1 is modeled by:

$$\log_{10} P_1^S = A_1 - \frac{B_1}{T + C_1}. \quad (8)$$

The coefficients in eq 8 for TFE are ($A_1$=7.90353, $B_1$=2012.94, $C_1$=1.2044) and $CO_2$ are ($A_1$=12.3312, $B_1$=4759.46, $C_1$=156.462), and it is assumed that eq 8 holds even above VLE (vapor liquid equilibrium) critical temperature $T_c$ as an extrapolated hypothetical vapor pressure.

The present solubility model contains maximum four adjustable parameters: $\tau_{12}^{(0)}$, $\tau_{12}^{(1)}$, $\tau_{21}^{(0)}$, and $\tau_{21}^{(1)}$. These parameters have been determined using non-linear least-squares analysis with an objective function of: $\Sigma_{i=1}^{N}(1-P_{obs}(i)/P_{calc}(i))^2$ for N data points. Optimal values for these parameters for TFE are $\tau_{12}^{(0)}$=1.0662, $\tau_{12}^{(1)}$=339.40 K, $\tau_{21}^{(0)}$=4.5270, and $\tau_{21}^{(1)}$=-805.60 K. Optimal values for these parameters for $CO_2$ are $\tau_{12}^{(0)}$=-4.663, $\tau_{12}^{(1)}$=2806.8 K, $\tau_{21}^{(0)}$=1.0656, and $\tau_{21}^{(1)}$=-812.37 K.

Although the infinite dilution state is only a limited (or extrapolated) state of actual solutions, the thermodynamic properties at such a state provide important physical/chemical understandings about solute and solvent interactions. Activity coefficients at infinite dilution, $\gamma_1^\infty$, of TFE and $CO_2$ in [bmim][$PF_6$] can be derived from eq 1 by setting $x_1$=0 and $x_2$=1.

$$\ln \gamma_1^\infty = \tau_{21} + \tau_{12} G_{12}. \quad (11)$$

Table 1 provides temperature (T), the saturated vapor pressure ($P_i^S$), the $2^{nd}$ virial coefficient ($B_{11}$), and the activity coefficient at infinite dilution ($\gamma_1^\infty$) for TFE and $CO_2$ in [bmim][$PF_6$].

TABLE 1

| Gas | T (K) | $P_i^S$ (MPa) | $B_{11}$ (cm$^3$ mol$^{-1}$) | $\gamma_1^\infty$ |
|---|---|---|---|---|
| TFE | 287.92 | 2.5634 | −673.62 | 23.61 |
| TFE | 328.29 | 6.0156 | −612.58 | 31.58 |
| $CO_2$ | 283.15 | 4.4917 | −138.57 | 1.04 |
| $CO_2$ | 298.15 | 6.4361 | −123.01 | 1.22 |
| $CO_2$ | 323.15 | 11.1077 | −102.06 | 1.49 |
| $CO_2$ | 348.15 | 18.1611 | −85.49 | 1.71 |

These activity coefficients at infinite dilution $\gamma_1^\infty$ were used to calculate the selectivity ($\alpha_{ij}$):

$$\alpha_{ij} = \frac{\gamma_i^\infty}{\gamma_j^\infty}$$

where components i and j are present at an infinite degree of dilution in the entrainer [bmim][$PF_6$] and i can represent TFE, and j can represent $CO_2$. In order to achieve separation, a selectivity of greater than about 1.0 is preferred. The selectivities ($\alpha_{ij}$) in Table 2 show that the use of [bmim][PF$_6$] as an entrainer will separate TFE and CO$_2$ with a selectivity of greater than 20 over a temperature from 283.15 to 348.15 K.

TABLE 2

| T (K) | $\gamma_i^\infty$ | $\gamma_j^\infty$ | $\alpha_{ij}$ |
| --- | --- | --- | --- |
| 283.15 | 22.66 | 1.04 | 21.8 |
| 298.15 | 25.62 | 1.22 | 21.0 |
| 323.15 | 30.56 | 1.49 | 20.5 |
| 348.15 | 35.49 | 1.71 | 20.7 |

EXAMPLE 2

Separation of a Mixture Comprising Tetrafluoroethylene and Carbon Dioxide

An Aspen Plus® process simulation was used to model the separation of a mixture containing tetrafluoroethylene (TFE) and carbon dioxide (CO$_2$) by extractive distillation using [bmim][PF$_6$] as the entrainer. The Aspen flowsheet used for this simulation consists of an extraction column modeled with RadFrac and a single stage stripping unit modeled as a flash drum for the regeneration of the ionic liquid (IL), which is recycled back into the main column as shown in FIG. 1.

The immeasurable vapor pressure of the ionic liquid was taken into consideration by fitting the extended Antoine equation value close to zero. The ionic liquid was treated as a non-dissociating component and assumption of an ideal vapor phase was made, therefore, the investigated vapor-liquid equilibrium (VLE) data could be described by the liquid concentration and activity coefficient. Nonrandom two-liquid (NRTL) binary interaction parameters [S. I., Sandler, Chemical and Engineering Thermodynamics, 3$^{rd}$ Edition (1999) John Wiley and Sons, Inc., New York, Chapter 7] between the components and the ionic liquid were generated using (P, T, x) data obtained from solubility experiments (see Examples 3 and 4 for solubility data for TFE and CO$_2$, respectively, in [bmim][PF$_6$]). Aspen was used to regress the NRTL parameters from the (P, T, x) data.

The extraction column consists of 20 theoretical stages, including the partial condenser and reboiler, and operates at 793 kPa (115 psia). The feed is a 50 wt % TFE and 50 wt % CO$_2$ at 25° C., which is fed into the column at stage 9. The ionic liquid is fed at approximately a 40:1 mass ratio relative to the feed through the second stage of the column at 25° C. The column operates with a mass reflux ratio of 1.5. As shown in Table 3, 98% of the TFE fed into the main column is recovered as a vapor distillate from this column, with a purity of 99.73 wt %. The remaining TFE and essentially all of the CO$_2$ leave out the column bottom along with the ionic liquid.

The bottoms stream from the extraction column is sent to a flash drum operating at 2 psia and 180° C. This flash strips the CO$_2$ and residual TFE from the ionic liquid being recycled, reducing its impurity level down to nominally 300 ppmw CO$_2$ and 1 ppmw TFE.

TABLE 3

| Aspen Results | |
| --- | --- |
| Extraction Column Feeds | |
| Ionic Liquid (IL) (kg/hr) | 4000 |
| TFE/CO$_2$ (kg/hr) | 100 |
| TFE/CO$_2$ Composition | 50 wt % TFE/50 wt % CO2 |

TABLE 3-continued

| Aspen Results | |
| --- | --- |
| TFE/CO$_2$ gas mixture Temp. (K) | 298.15 |
| Ionic Liquid (IL) Temp. (K) | 298.15 |
| Extraction Column | |
| Distillate, overhead (kg/hr) | 49 |
| Distillate purity (wt % TFE) | 99.73% |
| Product Yield | 98% |
| Bottoms flow (kg/hr) | 4051 |
| Theoretical stages | 20 |
| Operating pressure (psia) | 115 |
| Reflux ratio (mass basis) | 1.5 |
| Ionic Liquid stage | 2 |
| TFE/CO$_2$ Feed stage | 9 |
| Condenser Temperature (K) | 245.85 K |
| Reboiler Temperature (K) | 332.55 K |
| Condenser duty (BTU/hr) | −14,300 |
| Reboiler duty (BTU/hr) | 195,000 |
| Stripper Flash Tank | |
| Operating pressure (psia) | 2 |
| Operating Temperature (K) | 453.15 |
| CO$_2$, Overhead purity ($x_{W2}$) | 99.1% |
| Ionic Liquid, Recycle (kg/hr) | 4000.02 kg/hr |
| Ionic Liquid, Recycle purity | 99.97% |
| Heat duty (BTU/hr) | 700,000 |
| Solvent Cooler | |
| Heat Duty (BTU/hr) | −871,000 |

Examples 3 and 4 provide solubility results for tetrafluoroethylene (TFE) and carbon dioxide (CO$_2$), respectively. These data are used for calculating the activity coefficient at infinite dilution ($\gamma_1^\infty$) as shown in Example 1 and the NRTL parameters for ASPEN® process modeling in Example 2.

EXAMPLE 3

Solubility of Tetrafluoroethylene (TFE) in 1-Butyl-3-methylimidazolium hexafluorophosphate A solubility study was made at temperatures of 14.77 and 55.14° C. over a pressure range from 0 to about 1.4 MPa where the solubilities ($x_{meas.}$) were measured using a volumetric view cell. Tables 4a and 4b provide data for T, P, and $x_{meas}$ at temperatures of 14.77 and 55.14° C., respectively.

TABLE 4a

| T (° C.) | P (MPa) | $x_{meas.}$ (mole %) |
| --- | --- | --- |
| 14.77 | 0.0713 | 0.2494 |
| 14.77 | 0.1762 | 0.6096 |
| 14.77 | 0.3020 | 1.0300 |
| 14.77 | 0.4473 | 1.4890 |
| 14.77 | 0.5837 | 1.9100 |
| 14.77 | 0.7400 | 2.3770 |
| 14.77 | 0.9012 | 2.8450 |
| 14.77 | 1.0463 | 3.3100 |

TABLE 4b

| T (° C.) | P (MPa) | $x_{meas.}$ (mole %) |
| --- | --- | --- |
| 55.14 | 0.1398 | 0.2938 |
| 55.14 | 0.2813 | 0.5711 |
| 55.14 | 0.4316 | 0.8571 |
| 55.14 | 0.5680 | 1.1110 |
| 55.14 | 0.7044 | 1.3590 |
| 55.14 | 0.8526 | 1.6250 |
| 55.14 | 0.9903 | 1.8640 |
| 55.14 | 1.1322 | 2.1050 |

TABLE 4b-continued

| T (° C.) | P (MPa) | $x_{meas.}$ (mole %) |
|---|---|---|
| 55.14 | 1.2727 | 2.3360 |
| 55.14 | 1.4192 | 2.5730 |

EXAMPLE 4

Solubility of Carbon Dioxide ($CO_2$) in 1-Butyl-3-methylimidazolium hexafluorophosphate A solubility study was made at temperatures of 10.0, 25.0, 50.0, and 75.0° C. over a pressure range from 0 to about 2.0 MPa where the solubilities ($x_{meas.}$), were measured using a gravimetric microbalance. Tables 5a, 5b, 5c, and 5d provide data for T, P, and $x_{meas}$ at temperatures of 10.0, 25.0, 50.0, and 75.0° C., respectively.

TABLE 5a

| T (° C.) | P (MPa) | $x_{meas.}$ (mole %) |
|---|---|---|
| 9.9  | 0.0097 | 0.4 |
| 9.9  | 0.0501 | 1.6 |
| 9.9  | 0.1002 | 2.9 |
| 10.4 | 0.3996 | 10.2 |
| 10.6 | 0.6996 | 16.7 |
| 10.5 | 1.0000 | 22.4 |
| 8.9  | 1.3003 | 28.4 |
| 9.9  | 1.4998 | 30.9 |
| 9.9  | 1.9998 | 37.9 |

TABLE 5b

| T (° C.) | P (MPa) | $x_{meas.}$ (mole %) |
|---|---|---|
| 24.9 | 0.0102 | 0 |
| 24.9 | 0.0502 | 0.9 |
| 24.9 | 0.1002 | 1.8 |
| 25.0 | 0.3996 | 7.2 |
| 25.0 | 0.7000 | 12.2 |
| 24.9 | 0.9994 | 16.7 |
| 24.9 | 1.2999 | 20.8 |
| 24.9 | 1.4994 | 23.3 |
| 24.9 | 1.9992 | 29.1 |

TABLE 5c

| T (° C.) | P (MPa) | $x_{meas.}$ (mole %) |
|---|---|---|
| 50.1 | 0.0102 | 0.2 |
| 50.0 | 0.0503 | 0.6 |
| 50.0 | 0.1002 | 1.2 |
| 50.1 | 0.3996 | 4.7 |
| 50.0 | 0.7000 | 7.9 |
| 50.0 | 0.9998 | 10.9 |
| 50.0 | 1.3002 | 13.6 |
| 50.1 | 1.5003 | 15.5 |
| 50.0 | 1.9998 | 19.7 |

TABLE 5d

| T (° C.) | P (MPa) | $x_{meas.}$ (mole %) |
|---|---|---|
| 75.0 | 0.0102 | 0.1 |
| 74.9 | 0.0501 | 0.2 |

TABLE 5d-continued

| T (° C.) | P (MPa) | $x_{meas.}$ (mole %) |
|---|---|---|
| 74.9 | 0.1000 | 0.7 |
| 74.9 | 0.3997 | 3.2 |
| 74.9 | 0.7000 | 5.6 |
| 74.8 | 1.0002 | 7.8 |
| 75.0 | 1.3003 | 9.9 |
| 74.9 | 1.4999 | 11.3 |
| 75.1 | 1.9995 | 14.9 |

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

What is claimed is:

1. A kit comprising a first container that is pressurized and contains a mixture of TFE and $CO_2$, a second container that contains one or more ionic liquids, and a connector to connect the first container to the second container;

wherein the second container comprises an inlet from which the contents of the first container may be passed through the contents of the second container to a release for TFE at an outlet; and wherein the second container comprises means for contacting the contents of the first container with the contents of the second container within the second container.

2. A kit according to claim 1 wherein an ionic liquid has a cation selected from the group consisting of the following eleven cations:

Pyridinium     Pyridazinium

Pyrimidinium   Pyrazinium

-continued

Imidazolium    Pyrazolium

Thiazolium    Oxazolium

Triazolium    Phosphonium    Ammonium wherein $R^1$, $R^2$, $R^3$, $R^4$, $R^5$ and $R^6$ are independently selected from the group consisting of:
(i) H
(ii) halogen
(iii) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH;
(iv) —$CH_3$, —$C_2H_5$, or a $C_3$ to $C_{25}$ straight-chain, branched or cyclic alkane or alkene group comprising one to three heteroatoms selected from the group consisting of O, N and S, and optionally substituted with at least one member selected from the group consisting of Cl, Br, F, I, OH, $NH_2$ and SH;
(v) A $C_6$ to $C_{20}$ unsubstituted aryl, or a $C_6$ to $C_{25}$ unsubstituted heteroaryl, group having one to three heteroatoms independently selected from the group consisting of O, N and S; and
(vi) A $C_6$ to $C_{25}$ substituted aryl, or a $C_6$ to $C_{25}$ substituted heteroaryl, group having one to three heteroatoms independently selected from the group consisting of O, N and S; and wherein said substituted aryl or substituted heteroaryl group has one to three substituents independently selected from the group consisting of:
(1) —$CH_3$, —$C_2H_5$, or a $C_3$ to $C_{25}$ straight-chain, branched or cyclic alkane or alkene group, optionally substituted with at least one member selected from the group consisting of Cl, Br, F I, OH, $NH_2$ and SH,
(2) OH,
(3) $NH_2$, and
(4) SH;
$R^7$, $R^8$, $R^9$, and $R^{10}$ are independently selected from the group consisting of:
(vii) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH;

(viii) —$CH_3$, —$C_2H_5$, or a $C_3$ to $C_{25}$ straight-chain, branched or cyclic alkane or alkene group comprising one to three heteroatoms selected from the group consisting of O, N and S, and optionally substituted with at least one member selected from the group consisting of Cl, Br, F, I, OH, $NH_2$ and SH;
(ix) a $C_6$ to $C_{25}$ unsubstituted aryl, or a $C_6$ to $C_{25}$ unsubstituted heteroaryl, group having one to three heteroatoms independently selected from the group consisting of O, N and S; and
(x) a $C_6$ to $C_{25}$ substituted aryl, or a $C_6$ to $C_{25}$ substituted heteroaryl, group having one to three heteroatoms independently selected from the group consisting of O, N and S; and wherein said substituted aryl or substituted heteroaryl group has one to three substituents independently selected from the group consisting of:
(1) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH,
(2) OH,
(3) $NH_2$, and
(4) SH; and
wherein optionally at least two of $R^1$, $R^2$, $R^3$, $R^4$, $R^5$, $R^6$, $R^7$, $R^8$, $R^9$, and $R^{10}$ can together form a cyclic or bicyclic alkanyl or alkenyl group.

3. A kit according to claim 2 wherein at least one of $R^1$, $R^2$, $R^3$, $R^4$, $R^5$, $R^6$, $R^7$, $R^8$, $R^9$, and $R^{10}$ comprises $F^-$.

4. A kit according to claim 1 wherein an iconic liquid comprises an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, and any fluorinated anion.

5. A kit according to claim 2 wherein an ionic liquid comprises an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, and any fluorinated anion.

6. A kit according to claim 1 wherein an ionic liquid comprises an anion selected from the group consisting of $[BF_4]^-$, $[BF_3CF_3]^-$, $[BF_3C_2F_5]^-$, $[PF_6]^-$, $[PF_3(C_2F_5)_3]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$.

7. A kit according to claim 2 wherein an ionic liquid comprises an anion selected from the group consisting of $[BF_4]^-$, $[BF_3CF_3]^-$, $[BF_3C_2F_5]^-$, $[PF_6]^-$, $[PF_3(C_2F_5)_3]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$.

8. A kit according to claim 1 wherein an ionic liquid comprises 1-butyl-3-methylimidazolium as the cation; and comprises an anion selected from the group consisting of $[BF_4]^-$, $[BF_3CF_3]^-$, $[BF_3C_2F_5]^-$, $[PF_6]^-$, $[PF_3(C_2F_5)_3]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $[CH_3OSO_3]^-$.

9. A kit according to claim 1 wherein an ionic liquid comprises 1-ethyl-3-methylimidazolium as the cation, and comprises an anion selected from the group consisting of $[(CF_3CF_2SO_2)_2N]^-$, $[PF_6]^-$ and $[HCF_2CF_2SO_3]^-$.

10. A kit according to claim 1 wherein an ionic liquid comprises 1,3-dimethylimidazolium as the cation; and comprises an anion selected from the group consisting of $[BF_4]^-$, $[BF_3CF_3]^-$, $[BF_3C_2F_5]^-$, $[PF_6]^-$, $[PF_3(C_2F_5)_3]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $[CH_3OSO_3]^-$.

* * * * *